United States Patent
Xia et al.

(10) Patent No.: US 9,010,172 B2
(45) Date of Patent: Apr. 21, 2015

(54) DETECTION SYSTEM AND HUMIDITY DETECTION METHOD FOR DETECTING VOLATILE ORGANIC COMPOUND

(75) Inventors: Keyu Xia, Guangdong (CN); Jiaming Zhang, Guangdong (CN)

(73) Assignee: Dongguan City Simplewell Technology Co., Ltd., Guangdong (CN)

( * ) Notice: Subject to any disclaimer, the term of this patent is extended or adjusted under 35 U.S.C. 154(b) by 337 days.

(21) Appl. No.: 13/643,081

(22) PCT Filed: Nov. 18, 2010

(86) PCT No.: PCT/CN2010/078862
§ 371 (c)(1),
(2), (4) Date: Oct. 24, 2012

(87) PCT Pub. No.: WO2011/150633
PCT Pub. Date: Dec. 8, 2011

(65) Prior Publication Data
US 2013/0036794 A1     Feb. 14, 2013

(30) Foreign Application Priority Data
Jun. 1, 2010   (CN) .......................... 2010 1 0192127

(51) Int. Cl.
*G01N 25/66*     (2006.01)
*G01N 33/00*     (2006.01)
(52) U.S. Cl.
CPC ............ *G01N 25/66* (2013.01); *G01N 33/0047* (2013.01)
(58) Field of Classification Search
CPC ......... G01N 1/22; G01N 25/66; G01N 33/00; G01N 33/0047
USPC .......... 73/19.01, 23.2, 25.04, 29.01, 73/31.01–31.03, 866; 220/565
See application file for complete search history.

(56) References Cited

U.S. PATENT DOCUMENTS

2002/0071786 A1    6/2002  Schreiber, Jr. et al.

FOREIGN PATENT DOCUMENTS

| CN | 101025423 A | 8/2007 |
| CN | 101285811 A | 10/2008 |
| CN | 201322745 Y | 10/2009 |
| CN | 201322745 Y * | 10/2009 |
| JP | 2009098006 A | 5/2009 |
| JP | 2009229198 A | 10/2009 |

OTHER PUBLICATIONS

English translation of CN 201322745 Y to Xie.*

* cited by examiner

Primary Examiner — Laura Martin
Assistant Examiner — Irving A Campbell

(57) ABSTRACT

Detection system and humidity detection method for detecting volatile organic compound comprises a device for introducing clean air and a controller, wherein the device for introducing clean air is connected with a test chamber; a test chamber sheath is sleeved outside the test chamber; the test chamber is provided with a temperature sensor for detecting the temperature in the test chamber, a high-temperature test exhaust device is connected with a high-temperature exhaust pipeline of the test chamber, and a low-temperature test exhaust device is connected with a low-temperature exhaust pipeline of the test chamber; a pipeline connecting the test chamber with the low-temperature test exhaust device is also provided with a dew point sensor for detecting dew point of the air in the low-temperature exhaust pipeline; and the temperature sensor and the dew point sensor are connected with the controller.

10 Claims, 1 Drawing Sheet

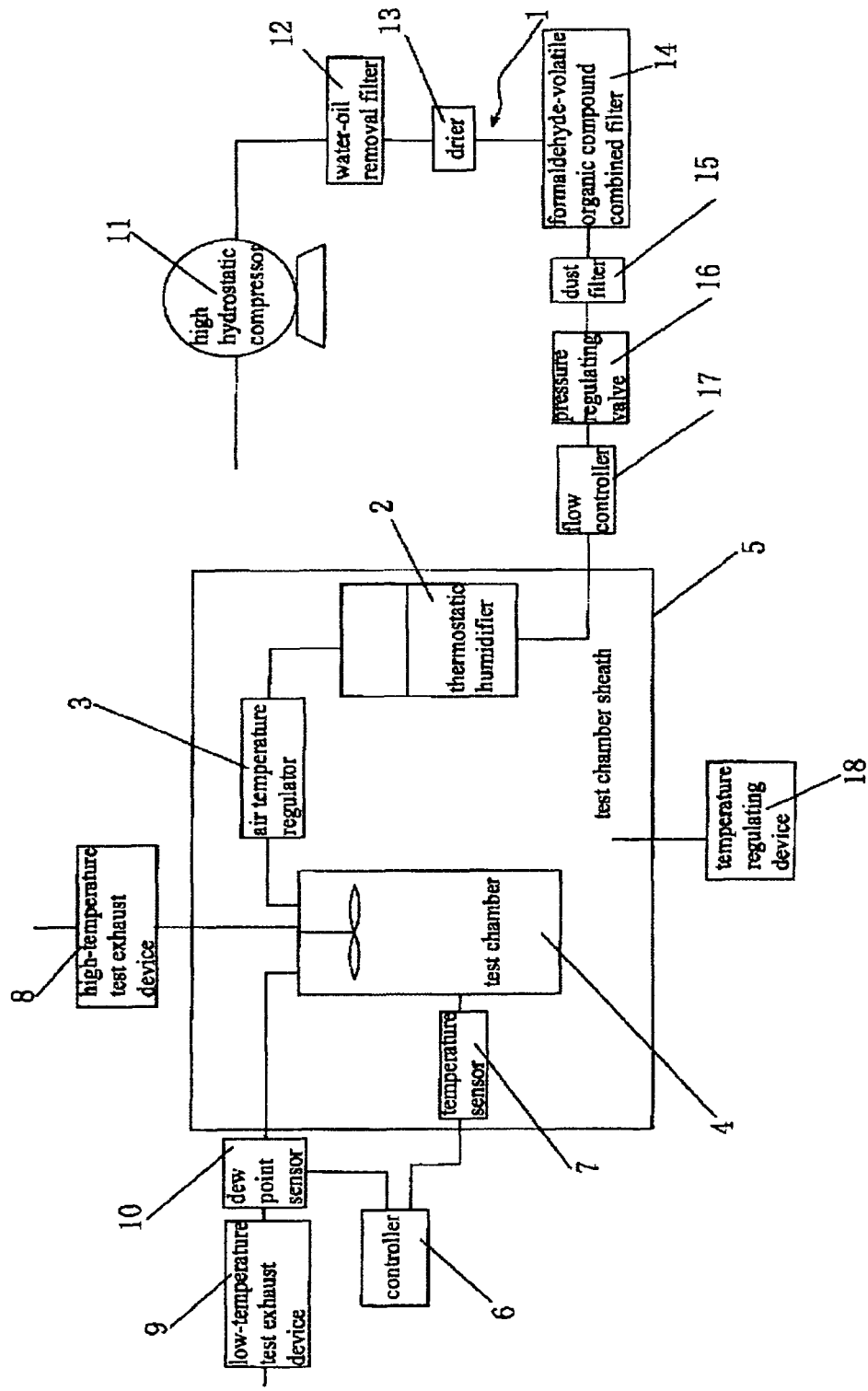

DETECTION SYSTEM AND HUMIDITY DETECTION METHOD FOR DETECTING VOLATILE ORGANIC COMPOUND

BACKGROUND OF THE INVENTION

The present invention relates to an environmental testing system, and more specifically to a detection system for detecting volatile organic compounds and a method for detecting humidity with this detection system, wherein the detection system can be used for low and/or high temperature tests, and automatically regulate humidity, temperature and air exchange rate of the test environment as required by the test environment.

With the continuous improvement of people's living standard, people's demand for environmental quality has also been greatly improved, especially for the environmental indicators of the living environment, so as to protect the human body from the injury of formaldehyde and other toxic substances. However, many indoor materials and products contain such toxic substances as formaldehyde. In order to secure health of the human body, the release rate and release characteristics of such toxic substances as formaldehyde contained in the indoor materials and products need to be detected, especially to be detected in a certain high-temperature environment, so as to obtain the qualified indoor materials and products and make people have a good living environment. Therefore, a detection environment meeting the requirements needs to be provided, so as to improve accuracy of the detection. During detection by the detection system, the temperature and humidity in the test chamber need to be detected and controlled, which is conventionally achieved by installing a temperature sensor and a humidity sensor in the test chamber to detect and control the temperature and humidity in the test chamber. The humidity sensor is prone to damage during the high-temperature detection, which results in high maintenance cost and inconvenience in use.

BRIEF SUMMARY OF THE INVENTION

A purpose of the present invention is to overcome the above defects in the prior art: The present invention provides a detection system for detecting volatile organic compounds, which can accurately control temperature and humidity in the test chamber, enables temperature and humidity in the test chamber to be uniform, can perform low-temperature detection and high-temperature detection, has low maintenance cost and is convenient to use, and can effectively meet the requirements of the test environment.

Another purpose of the present invention is to overcome the above defects in the prior art: The present invention provides a humidity detection method using the detection system for detecting volatile organic compounds, which enables the detection system to be used both for the low-temperature detection and for the high-temperature detection.

In order to achieve the above purposes, the present invention provides the following technical solution: A detection system for detecting volatile organic compounds is provided, comprising a device for introducing clean air and a controller, wherein the device for introducing clean air is connected with a test chamber; a test chamber sheath is sleeved outside the test chamber; the test chamber is provided with a temperature sensor for detecting the temperature in the test chamber, a high-temperature test exhaust device connected with a high-temperature exhaust pipeline of the test chamber, and a low-temperature test exhaust device connected with a low-temperature exhaust pipeline of the test chamber; a pipeline connecting the test chamber with the low-temperature test exhaust device is also provided with a dew point sensor for detecting dew point of the air in the low-temperature exhaust pipeline; and the temperature sensor and the dew point sensor are connected with the controller.

The present invention provides a humidity detection method using the detection system for detecting volatile organic compounds, the method comprising the following steps:

A. inputting database into the controller, and recording the saturated-air-humidity water content or saturated air pressure corresponding to different temperature;

B. while doing a low temperature test, turning off the high-temperature test exhaust device, turning on the low-temperature test exhaust device, detecting temperature inside the test chamber with a temperature sensor installed on the test chamber for detecting the temperature inside the test chamber, and automatically searching in the controller for the saturated-air water content or the saturated air pressure corresponding to this temperature;

C. detecting the dew point temperature of the air in the low-temperature exhaust pipeline with the dew point sensor installed on the pipeline connecting the test chamber with the low-temperature test exhaust device for detecting the dew point of the air in the low-temperature exhaust pipeline, and automatically searching in the controller for the saturated-air water content or the saturated air pressure corresponding to this dew point temperature;

D. calculating relative humidity in the test chamber by multiplying a ratio of the saturated-air water content corresponding to the dew point temperature of the air in the low-temperature exhaust pipeline detected by the dew point sensor to the saturated-air water content or the saturated air pressure corresponding to the temperature in the test chamber detected by the temperature sensor by 100%; and E. while doing a high temperature test, turning off the low-temperature test exhaust device, and turning on the high-temperature test exhaust device to exhaust the gas.

The detection system and the humidity detection method for detecting volatile organic compounds according to the present invention have the following beneficial effects: The test chamber is provided with a temperature sensor for detecting the temperature in the test chamber, a high-temperature test exhaust device connected with a high-temperature exhaust pipeline of the test chamber, and a low-temperature test exhaust device connected with a low-temperature exhaust pipeline of the test chamber; a pipeline connecting the test chamber with the low-temperature test exhaust device is also provided with a dew point sensor for detecting dew point of the air in the low-temperature exhaust pipeline, and the temperature sensor and the dew point sensor are connected with the controller; while doing a low temperature test, detecting temperature inside the test chamber with a temperature sensor installed on the test chamber for detecting the temperature inside the test chamber, and automatically searching in the controller for the water content of the air corresponding to this temperature; detecting the dew point temperature of the air in the low-temperature exhaust pipeline with the dew point sensor installed on the pipeline connecting the test chamber with the low-temperature test exhaust device for detecting the dew point of the air in the low-temperature exhaust pipeline, and automatically searching in the controller for the water content of the air corresponding to this dew point temperature; calculating relative humidity in the test chamber by multiplying a ratio of the saturated-air water content corresponding to the dew point temperature of the air in the low-temperature exhaust pipeline detected by the dew point sensor to the water content of the air corresponding to the temperature in the test chamber detected by the temperature sensor by 100%; thus, the technical problem that the humidity sensor of the conventional detection system is easy to be damaged during high-temperature detection is effectively solved, enabling the detection system to be used both for the low-temperature detection and for the high-temperature detection, making the detection system have low maintenance cost and be convenient to use.

The detection system and the humidity detection method for detecting volatile organic compounds according to the present invention will further be described below with reference to drawings and examples:

BRIEF DESCRIPTION OF THE DRAWINGS

FIG. 1 is a structural schematic view of the detection system of the present invention for detecting volatile organic compounds.

DETAILED DESCRIPTION OF THE INVENTION

The detection system and the humidity detection method for detecting volatile organic compounds according to the present invention have the following most preferred examples which, however, will not limit the extent of protection of the present invention.

Example 1

As shown in FIG. 1, a detection system for detecting volatile organic compounds is provided, comprising a device for introducing clean air 1 and a controller 6, wherein the device for introducing clean air 1 is connected with a test chamber 4; a test chamber sheath 5 is sleeved outside the test chamber 4; the test chamber 4 is provided with a temperature sensor 7 for detecting the temperature in the test chamber 4, a high-temperature test exhaust device 8 connected with a high-temperature exhaust pipeline of the test chamber 4, and a low-temperature test exhaust device 9 connected with a low-temperature exhaust pipeline of the test chamber 4; a pipeline connecting the test chamber 4 with the low-temperature test exhaust device 9 is also provided with a dew point sensor 10 for detecting dew point of the air in the low-temperature exhaust pipeline; and the temperature sensor 7 and the dew point sensor 10 are connected with the controller 6; the test chamber 4 is made of mirror stainless steel, glass and PFA, with the corner designed in an arc shape and polished after full welding.

A pipeline connecting the device for introducing clean air 1 with the test chamber 4 is further connected with a thermostatic humidifier 2 and an first air temperature regulator 3.

The first air temperature regulator 3 is a shell-and-tube air regulator.

The device for introducing clean air 1 is composed of a high hydrostatic compressor 11, a water-oil removal filter 12, a drier 13, a formaldehyde-volatile organic compound combined filter 14, a dust filter 15, a pressure regulating valve 16, and a flow controller 17 sequentially connected on an admission pipeline.

The thermostatic humidifier 2 is provided inside with multilayer orifice plates at intervals to make air and water mixed sufficiently, effectively dissolve and remove formaldehyde in the gas, and meanwhile make the gas become a water-saturated gas.

The thermostatic humidifier 2 is further provided inside with an evaporator and a heater, and installed outside or inside the test chamber sheath 5.

The first air temperature regulator 3 is a gas container arranged in a water tank, which is provided inside with an evaporator and a heater and controls water temperature in the water tank through a controller, the first air temperature regulator 3 being installed outside or inside the test chamber sheath 5.

The test chamber 4 is further provided with a second air temperature regulator, which controls the temperature in the test chamber 4 through the controller 6.

The first air temperature regulator 3 can also be a gas container provided inside with a heater, and controls gas temperature in the gas container through the controller.

The test chamber sheath 5 is further provided with a temperature regulating device 18 for regulating the temperature inside the test chamber sheath 5.

This system calculates relative humidity in the test chamber by multiplying a ratio of the saturated-air water content corresponding to the dew point temperature of the air in the low-temperature exhaust pipeline detected by the dew point sensor 10 to the water content of the air corresponding to the temperature in the test chamber detected by the temperature sensor 7 by 100%, thus effectively solving the technical problem that the humidity sensor of the conventional detection system is easy to be damaged during high-temperature detection, enabling the detection system to be used both for the low-temperature detection and for the high-temperature detection.

Example 2

The present invention provides a humidity detection method using the detection system for detecting volatile organic compounds, the method comprising the following steps:

A. inputting database into the controller 1, and recording the saturated-air-humidity water content or saturated air pressure corresponding to different temperature;

B. while doing a low temperature test, turning off the high-temperature test exhaust device 8, turning on the low-temperature test exhaust device 9, detecting temperature inside the test chamber 4 with a temperature sensor 7 installed on the test chamber 4 for detecting the temperature inside the test chamber 4, and automatically searching in the controller 6 for the saturated-air water content or the saturated air pressure corresponding to this temperature;

C. detecting the dew point temperature of the air in the low-temperature exhaust pipeline with the dew point sensor 10 installed on the pipeline connecting the test chamber 4 with the low-temperature test exhaust device 9 for detecting the dew point of the air in the low-temperature exhaust pipeline, and automatically searching in the controller 6 for the saturated-air water content or the saturated air pressure corresponding to this dew point temperature;

D. calculating relative humidity in the test chamber 4 by multiplying a ratio of the saturated-air water content corresponding to the dew point temperature of the air in the low-temperature exhaust pipeline detected by the dew point sensor 10 to the saturated-air water content or the saturated air pressure corresponding to the temperature in the test chamber 4 detected by the temperature sensor 7 by 100%; and E. while doing a high temperature test, turning off the low-temperature test exhaust device 9, and turning on the high-temperature test exhaust device 8 to exhaust the gas.

The above examples are the preferred embodiments of the present invention. However, the embodiments of the present invention are not restricted to the above examples. Any other modification, decoration, substitution, combination and simplification, so long as not departing from the spirit of the present invention, shall be an equivalent replacement and fall within the extent of protection of the present invention.

What is claimed is:

1. A detection system for detecting volatile organic compounds, comprising a device for introducing clean air (1) and a test chamber (4) connected with the device for introducing clean air (1), a test chamber sheath (5) being sleeved outside the test chamber (4), characterized in that: the detection system further includes a controller (6); the test chamber (4) is provided with a temperature sensor (7) for detecting temperature in the test chamber (4), a high-temperature test exhaust device (8) connected with a high-temperature exhaust pipeline of the test chamber (4), and a low-temperature test exhaust device (9) connected with a low-temperature exhaust pipeline of the test chamber (4); a pipeline connecting the test chamber (4) with the low-temperature test exhaust device (9) is also provided with a dew point sensor (10) for detecting dew point of the air in the low-temperature exhaust pipeline; and the temperature sensor (7) and the dew point sensor (10) are connected with the controller (6).

2. The detection system for detecting volatile organic compounds according to claim 1, characterized in that: the device for introducing clean air (1) is composed of a high hydrostatic compressor (11), a water-oil removal filter (12), a drier (13), a formaldehyde-volatile organic compound combined filter (14), a dust filter (15), a pressure regulating valve (16), and a flow controller (17) sequentially connected on an admission pipeline.

3. The detection system for detecting volatile organic compounds according to claim 1, characterized in that: a pipeline connecting the device for introducing clean air (1) with the test chamber (4) is further connected with a thermostatic humidifier (2) and first air temperature regulator (3).

4. The detection system for detecting volatile organic compounds according to claim 1, characterized in that: the thermostatic humidifier (2) is provided inside with multilayer orifice plates at intervals to make air and water mixed sufficiently, effectively dissolve and remove formaldehyde in the gas, and meanwhile make the gas become a water-saturated gas.

5. The detection system and humidity detection method for detecting volatile organic compounds according to claim 4, characterized in that: the thermostatic humidifier (2) is further provided inside with an evaporator and a heater, and installed outside or inside the test chamber sheath (5).

6. The detection system for detecting volatile organic compounds according to claim 3, characterized in that: the first air temperature regulator (3) is a gas container arranged in a water tank, which is provided inside with an evaporator and a heater and controls water temperature in the water tank through a controller, the first air temperature regulator (3) being installed outside or inside the test chamber sheath (5).

7. The detection system for detecting volatile organic compounds according to claim 3, characterized in that: the first air temperature regulator (3) can also be a gas container provided inside with a heater, and controls gas temperature in the gas container through the controller.

8. The detection system for detecting volatile organic compounds according to claim 1, characterized in that: The test chamber (4) is further provided with a second air temperature regulator, which controls the temperature in the test chamber (4) through the controller (6).

9. The detection system and humidity detection method for detecting volatile organic compounds according to claim 1, characterized in that: the test chamber sheath (5) is further provided with a temperature regulating device (18) for regulating temperature inside the test chamber sheath (5).

10. A humidity detection method using the detection system for detecting volatile organic compounds according to claim 1, characterized in that: the method comprises the following steps:
A. inputting database into the controller (1), and recording saturated-air-humidity water content or saturated air pressure corresponding to different temperature;
B. while doing a low temperature test, turning off the high-temperature test exhaust device (8), turning on the low-temperature test exhaust device (9), detecting temperature inside the test chamber (4) with the temperature sensor (7) installed on the test chamber (4) for detecting the temperature inside the test chamber (4), and automatically searching in the controller (6) for the saturated-air water content or the saturated air pressure corresponding to this temperature;
C. detecting the dew point temperature of the air in the low-temperature exhaust pipeline with the dew point sensor (10) installed on the pipeline connecting the test chamber (4) with the low-temperature test exhaust device (9) for detecting the dew point of the air in the low-temperature exhaust pipeline, and automatically searching in the controller (6) for the saturated-air water content or the saturated air pressure corresponding to this dew point temperature;
D. calculating relative humidity in the test chamber (4) by multiplying a ratio of the saturated-air water content corresponding to the dew point temperature of the air in the low-temperature exhaust pipeline detected by the dew point sensor (10) to the saturated-air water content or the saturated air pressure corresponding to the temperature in the test chamber (4) detected by the temperature sensor (7) by 100%; and
E. while doing a high temperature test, turning off the low-temperature test exhaust device (9), and turning on the high-temperature test exhaust device (8) to exhaust the gas.

* * * * *